United States Patent [19]
Li et al.

[11] Patent Number: 5,637,505
[45] Date of Patent: Jun. 10, 1997

[54] METHOD TO PREPARE DYE-BASED REFERENCE MATERIAL

[75] Inventors: Jay J. Li, Franklin; Justin E. Davey, Norwood; David P. Swist, Marlboro; Liann Voo, West Roxbury, all of Mass.

[73] Assignee: Chiron Diagnostics Corporation, Walpole, Mass.

[21] Appl. No.: 447,168

[22] Filed: May 19, 1995

[51] Int. Cl.$^6$ ..................................... G01N 31/00
[52] U.S. Cl. ................... 436/8; 436/11; 436/15; 436/19
[58] Field of Search ................ 436/8, 11, 15, 436/19

[56] References Cited

U.S. PATENT DOCUMENTS

| | | | |
|---|---|---|---|
| 3,729,427 | 4/1973 | Louderback | 252/300 |
| 3,751,381 | 8/1973 | Megraw et al. | 436/15 X |
| 3,920,580 | 11/1975 | Mast | 436/15 X |
| 4,146,604 | 3/1979 | Kleinerman | 424/3 |
| 4,753,888 | 6/1988 | Chiang | 436/11 |
| 4,843,013 | 6/1989 | Chiang | 436/15 X |
| 4,945,062 | 7/1990 | Chiang | 436/11 |
| 4,962,039 | 10/1990 | Benedyk | 436/40 |
| 4,997,769 | 3/1991 | Lundsgaard | 436/66 |
| 5,013,666 | 5/1991 | Chiang | 436/11 |

FOREIGN PATENT DOCUMENTS

| | | |
|---|---|---|
| 0132399A1 | 1/1985 | European Pat. Off. . |
| 132399 | 1/1985 | European Pat. Off. . |
| 64-6865 | 1/1989 | Japan . |
| 2002516 | 2/1979 | United Kingdom . |

OTHER PUBLICATIONS

P. Dijkhuizen et al. *Clin. Chim. Acta* 1977, 78, 479–487.
R.J. Carrico et al. *J. Biol. Chem.* 1978, 253, 2386–2391.
A. Zwart et al. *J. Clin. Chem. Clin. Biochem.* 1981, 19, 457–462.
A. Zwart et al. *Clin. Chem.* 1981, 27, 1903–1907.
P.W. Wimberley et al. *Clin. Chem.* 1988, 34, 750–754.
Aldrich Chemical Company Catalog 1988, pp. 57, 675, 1370, and 1376.

*Primary Examiner*—Arlen Soderquist
*Attorney, Agent, or Firm*—Judith A. Roesler; Arthur S. Morgenstern; Robert P. Blackburn

[57] ABSTRACT

Provided is a method of preparing dye-based reference materials useful for calibrating or qualifying instrument systems that are diagnostic spectroscopically for hemoglobin and CO-ox fractions. The dye-based reference materials are non-proteinaceous and may be interpreted by CO-oximeter instrument systems as providing a spectrum substantially equivalent to the spectrum of blood, particularly with regard to hemoglobin and hemoglobin CO-ox fractions. Dye-based reference materials may be formulated to provide CO-ox fractions approximating those seen in a clinical setting, including normal physiological CO-ox fractions. The dye-based reference materials may be combined with other ingredients thus making the materials useful as references for pH and blood gas instruments and/or electrolyte instruments in addition to CO-oximeter instrument systems.

13 Claims, 7 Drawing Sheets

METHOD TO PREPARE DYE-BASED REFERENCE MATERIAL

FIELD OF INVENTION

This invention relates to a method of preparing dye-based reference materials useful for calibrating or qualifying instrument systems that are diagnostic spectroscopically for hemoglobin and CO-ox fractions. The reference materials may also be used in instrument systems that have, in addition to capability to measure CO-ox fractions, sensors for the measurement of blood pH, gas and other blood analytes including electrolyte concentrations and metabolite concentrations.

BACKGROUND OF THE INVENTION

Improvements in instrumentation have made the determination of blood pH, gas, electrolytes and CO-ox fractions relatively routine in clinical laboratories. Typically, pH and blood gas instruments measure blood pH, $pCO_2$, and $pO_2$. CO-oximeter instruments typically measure the total hemoglobin concentration (THb); the hemoglobin fractions such as oxyhemoglobin ($O_2$Hb); methemoglobin (MetHb); carboxyhemoglobin (COHb); and reduced hemoglobin (HHb) (collectively referred to herein as "CO-ox fractions"). Electrolyte instruments measure any number of blood electrolytes, including sodium, potassium, lithium, calcium, and so on. Instrument systems currently available may combine the measurement of blood pH, gases, electrolytes, various metabolites, and CO-ox fractions in one instrument for a comprehensive testing of the properties of blood, as is particularly useful in respiratory and pulmonary ailments. Vigorous therapeutic treatment is often dictated by such test results.

Quantitative determination of the various CO-ox fractions in clinical settings is desirable as CO-ox fractions relate to the loading of oxygen onto the hemoglobin of red blood cells circulating through the pulmonary capillaries. The actual amount of oxygen loaded onto the hemoglobin is determined not only by the concentration of total hemoglobin (THb), but also by the amount of non-oxygen-binding derivatives of hemoglobin such as carboxyhemoglobin (COHb) and methemoglobin (MetHb). Reduced hemoglobin (HHb) is an unoxygenated form of normal hemoglobin and elevations in the arterial fractional HHb indicate that lesser amounts of oxygen have been bound as a result of ventilation and/or perfusion defects.

Figure 1:
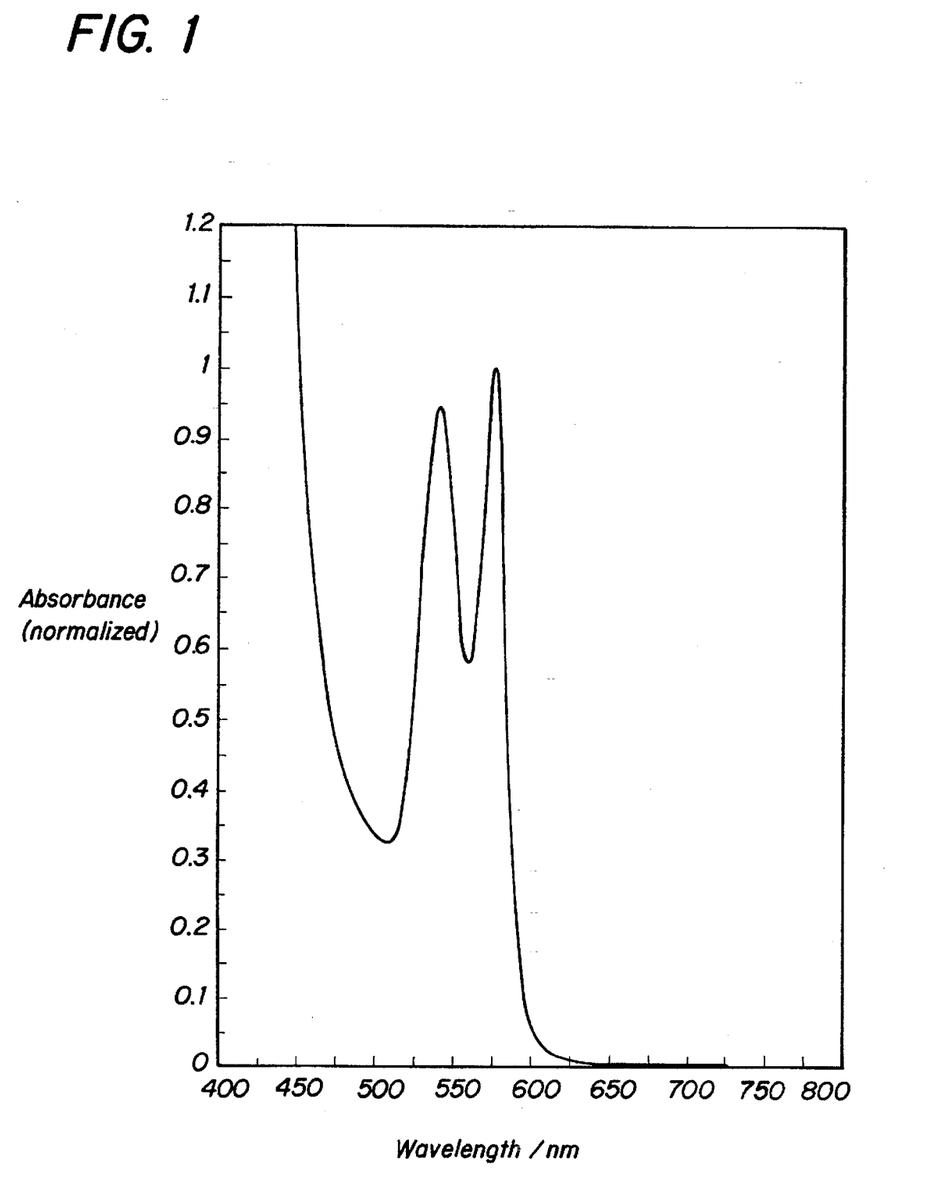
FIG. 1 shows the spectrum of blood.

Blood, hemoglobin and hemoglobin CO-ox fractions absorb visible light. A normal blood spectrum has a main absorption peak at 578 nm and decreases rapidly close to zero at wavelengths greater than about 610 nm as shown in FIG. 1. The second absorption peak of blood is at 542 nm. Absorbance maxima of hemoglobin derivatives are oxyhemoglobin, 541, 568–572 nm; reduced hemoglobin, 555 nm; carboxyhemoglobin, 537, 568–572 nm; and methemoglobin 540, 578, 630 nm.

Generally, optical type of CO-oximeters measure the absorbance of the blood sample at multiple wavelengths on the spectrum. Ultimately, based on the known CO-ox fraction absorption wavelengths regions, CO-oximeters analyze blood samples by the collection of absorption data at specific wavelengths. The data are then typically recorded and a process called multicomponent analysis is used to simultaneously calculate the concentrations of the each of hemoglobin CO-ox fraction present in the blood sample.

CO-oximeter instruments are typically designed to measure CO-ox fractions with values broader than the ranges observed in patient samples. For example, instruments may have the capability to measure CO-ox fractions in the defined instrument ranges of: about 4 to about 25 g/dL of THb, about 30% to about 98% oxyhemoglobin ($O_2$Hb); 0 to about 50% carboxyhemoglobin (COHb); 0 to about 40% methemoglobin (MetHb); and 0 to about 50% reduced hemoglobin (HHb), with all CO-ox fraction percentages herein based on the total amount of hemoglobin. Within the range of instrument capability is a clinically meaningful CO-ox fraction range and a normal physiological CO-ox fraction range. The clinically meaningful range is defined herein as: total hemoglobin 8 to 20 g/dL, 60 to 98% oxyhemoglobin ($O_2$Hb); 0 to 20% carboxyhemoglobin (COHb); 0 to about 20% methemoglobin (MetHb); and 0 to about 20% reduced hemoglobin (HHb). The normal physiological range is defined herein as: total hemoglobin 14 to 17 g/dL for men and 12 to 15 g/dL for women, oxyhemoglobin 94 to 98%, carboxyhemoglobin 0 to about 1% for nonsmoker, methemoglobin 0 to about 1.5%, and reduced hemoglobin from about 1 to about 5%.

Reference materials generally function to validate the performance of a diagnostic instrument. For CO-oximeter instrument systems, ideal quality control standard materials are formulated to provide pre-determined CO-ox fraction values not only within the broad instrument capability range, but also within the normal physiological range.

The prior art teaches two general types of CO-oximeter quality control standard materials. The first type are aqueous dye-based materials, where dyes are used in an attempt to match the spectrum of blood. The second type are blood-based materials, where the presence blood allows for the direct match of the spectrum of blood. Both types of materials have been associated with a variety of problems as discussed below.

In developing dye-based quality control standard materials for CO-ox instrument systems, to more closely approximate the spectrum of blood, combinations of dyes have been used. The combinations of dyes have been used because no single synthetic dye has a spectrum sufficiently similar to the absorption bands of a blood spectrum. Because the spectrum of blood has multiple distinctive bands of absorption, it is challenging to prepare a quality control standard material to mimic these characteristics. Although one dye might contribute an absorption characteristic that is present in the normal blood spectrum, it may also present other absorption characteristics that are dissimilar to blood at other portions of the spectrum.

Prior art methods teach dye combinations that only partially simulate blood's visible spectrum. Consequently, the CO-ox fraction values of the prior art quality control standard materials are often not clinically meaningful. For example, U.S. Pat. No. 4,843,013 teaches a combination of dyes for a CO-ox quality control standard, however, as shown in Cols. 6 and 7 of U.S. Pat. No. 4,843,013, the described quality control standard provides negative values for some of the CO-ox fractions. A negative value for a CO-ox fraction would never appear in a blood sample and thus these control standards have limited usefulness in qualifying CO-oximeters in a clinical setting. There has been a long-felt commercial need for dye-based quality control materials that may be formulated in a predictable manner to provide pre-determined clinically meaningful CO-ox fractions, particularly in the normal physiological range.

Blood-based reference materials provide clinically meaningful CO-ox fraction values, however, numerous limitations have been associated with using blood in the quality control standard materials. For example, a significant problem encountered by users of the proteinaceous blood-based materials is that blood-based materials are very susceptible to bacterial contamination and have a limited shelf life. Consequently, in most cases, users of blood-based materials must refrigerate the products during storage. Additionally, blood-based reference materials are generally classified as biohazardous materials, thus requiring the user to take additional safety precautions.

There is a need to provide non-proteinaceous dye-based reference materials that provide clinically and physiologically meaningful CO-ox fraction ranges.

SUMMARY OF THE INVENTION

According to the invention, a method to prepare a reference material for CO-oximeter instrument systems is provided, said method comprising (a) selecting a red dye having a main absorption maxima at a wavelength region between about 560 to about 580 nm to provide a basic spectrum; (b) modifying said main absorption maxima of said red dye by using a dye having an absorption maxima at a wavelength region between about 350 to about 450 nm; and (c) establishing a new relative baseline of said spectrum at wavelengths greater than about 640 nm and providing a sufficient absorbance at about 630 nm to provide a positive methemoglobin CO-ox fraction using one or more dyes.

Further provided is a reference material prepared according to said method, wherein said dyes are used in sufficient amounts to provide a reference material with CO-ox fractions falling within a range covering instrument capability. The method may also be used to prepare reference materials having CO-ox fractions with values falling within the defined clinical range or within the defined normal physiological range.

Also provided in one embodiment is a reference material comprising (a) a first dye having a main absorption maxima at a wavelength between about 560 to about 580 nm; (b) a second dye having an absorption maxima at a wavelength between about 350 to about 450 nm; and (c) a third dye having an absorption maxima at a wavelength between about 625 and about 640 nm; and (d) a fourth dye having an absorption maxima at a wavelength between about 700 to about 780 nm and an absorption band width of from about 150 to about 200 nm. The amounts of the dyes used in the materials may be adjusted to provide quality control materials with desired CO-ox fraction values.

Further provided is a method for quality control of CO-oximeter instrument systems comprising: (1) subjecting said instrument to a quality control standard material comprising (a) a first dye having a main absorption maxima at a wavelength between about 560 to about 580 nm; (b) a second dye having an absorption maxima at a wavelength between about 350 to about 450 nm; and (c) a third dye having an absorption maxima at a wavelength between about 625 and about 640 nm; and (d) a fourth dye having an absorption maxima at a wavelength between about 700 to about 780 nm and an absorption band width of from about 150 to about 200 nm; wherein said dyes are used in a sufficient amount to provide said control with a predetermined level of CO-ox fractions; (2) obtaining an instrument measurement of CO-ox fractions of said control; and (3) comparing said instrument measurement of said CO-ox fractions of said control with said predetermined level of CO-ox fractions to check the accuracy of said instrument.

The dye-based reference materials are non-proteinaceous and may be interpreted by CO-oximeter instrument systems as providing a spectrum substantially equivalent to the spectrum of blood, particularly with regard to total hemoglobin and hemoglobin CO-ox fractions. Using the inventive method of preparing the reference materials, dye-based reference materials may be formulated to provide CO-ox fractions approximating those seen in a clinical setting, including normal physiological values. These dye-based reference materials may also be combined with other ingredients which make the materials useful as reference materials for pH and blood gas instruments and/or electrolyte instruments in addition to CO-oximeter instruments.

DETAILED DESCRIPTION OF INVENTION

The present invention provides a method to formulate dye-based reference materials which mimic the spectrum of human blood when the reference materials are utilized in optical types of CO-oximeter instrument systems. The formulating method is described herein in distinct steps for purposes of clarity only. It should be understood that the steps set forth may be carried out in any order and may also be combined and carried out simultaneously. Additionally, the designation of first dye, second dye, and so on, is not intended to imply a specific order of dyes. The types of dyes selected, the amount of dyes utilized and the concentration of dyes described in these steps may be adjusted until the desired level of hemoglobin CO-ox fractions are obtained, as preferably determined by taking a reading from the specific CO-oximeter instrument that will be used with the reference material. All measurements of CO-ox fractions set forth herein were taken on Ciba Corning M270 CO-oximeters (as available from Ciba Corning Diagnostics Corp., Medfield, Mass. USA). All measurements of blood gas and electrolytes set forth herein were taken on Ciba Corning M288 Blood Gas Analyzers.

According to the invention, in step (a) a red dye is selected to provide a basic spectrum (also referred to herein as the first dye). In selecting the red dye, the general characteristics of the spectrum of normal blood should be considered. Normal blood has a spectrum with a main absorption peak at 578 nm which decreases rapidly close to zero at a wavelength greater than about 610 nm as shown in FIG. 1. The second absorption peak of blood is at approximately 542 nm. The absorbance maxima of the CO-ox fraction oxyhemoglobin is at the approximate wavelengths of 541 nm and 568–572 nm. As normal arterial blood has an oxyhemoglobin fraction greater than about 95%, the dye-based formulation should have a red dye with a spectrum similar to at least the general absorption features of oxyhemoglobin. The preferred red dyes in the invention have an absorption peak in the wavelength range from about 560 nm to about 580 nm. Further, particularly preferred red dyes exhibit minimal absorbance at a wavelength of greater than about 610 nm. Red dyes, such as, for example, sulforhodamine B, chlorophenol red, xylenol orange, sulforhodamine 101, etc., are currently preferred. Most preferably employed as the red dye is sulforhodamine B, which has an absorption maximum at approximately 566 nm in aqueous solution, a fairly narrow absorption bandwidth, and an absorbance which decreases to zero at about 620 nm, as shown as spectrum 1 in FIG. 2.

The single red dye does not exhibit a spectrum sufficiently similar to that of blood for purposes of obtaining clinically meaningful CO-ox fractions, as exemplified by the CO-ox fractions measured from 1.2 g/L of sulforhodamine B: THb 14 g/dL, $O_2$Hb −16%, COHb 105%, MetHb −2.5% and HHb 13.5%. As these values indicate, negative CO-ox fractions are obtained for the oxyhemoglobin and the methemoglobin.

Figure 2:
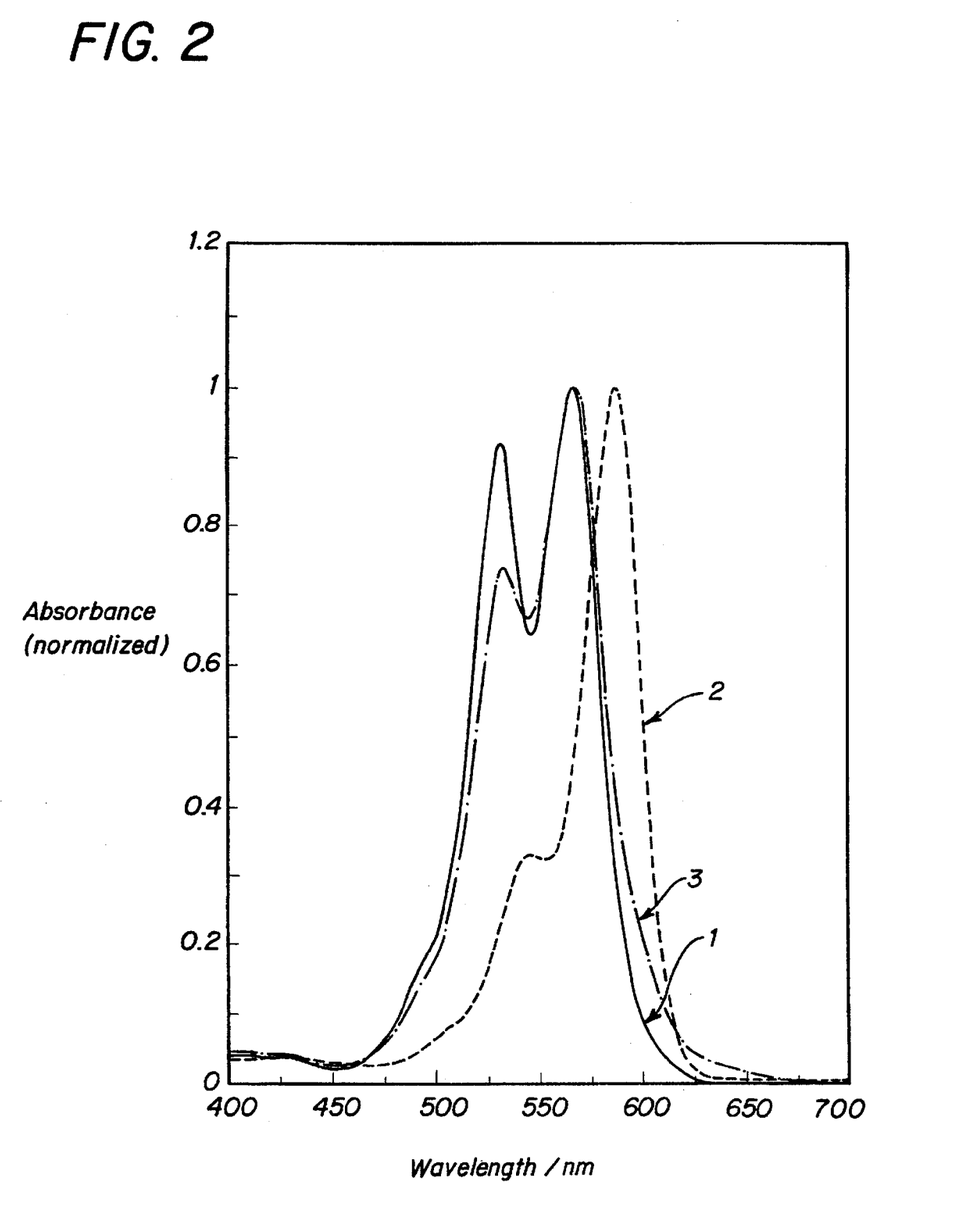
FIG. 2 shows the spectrums of single dyes and a dye combination that does not provide clinically meaningful CO-ox fractions. Spectrum 1 is taken from a sulforhodamine B solution. Spectrum 2 is taken from a sulforhodamine 101 solution. Spectrum 3 is taken from a solution containing 1 g/L sulforhodamine B and 0.1 g/L sulforhodamine 101.

One approach to alter the absorption peak of the red dye might be to introduce another red dye. In this approach, to shift the absorption peak to a longer wavelength, another red dye with absorption maximum wavelength greater than that of the first red dye could be utilized. Alternatively, to shift absorption peak to a shorter wavelength, another red dye with absorption maximum wavelength less than that of the first red dye could be utilized. A combination of the two red dyes would be predicted to result in a new overlapped maximum that would complement the required absorption features. However, as shown in FIG. 2, sulforhodamine B in aqueous solution provides a spectrum that does not have enough strength of absorbance at 570 to 585 nm because the absorption peak of the sulforhodamine B is located at a shorter wavelength than that of blood. Sulforhodamine 101 has an absorption peak at 587 nm. A combination of sulforhodamine B and sulforhodamine 101 shifts the absorption peak of sulforhodamine B and enhances the absorbance at 570 nm to 585 nm. In FIG. 2, spectrum 1 is sulforhodamine B, spectrum 2 is sulforhodamine 101, and spectrum 3 is the combination of 1 g/L sulforhodamine B and 0.1 g/L sulforhodamine 101. As shown in FIG. 2, absorbance of the two red dye combination at 570 to 585 nm is enhanced and results in the change of CO-ox fractions from negative values to positive values, e.g., 14 g/dL THb, 16% $O_2$Hb, 1% MetHb, 14% COHb and 69% HHb. The addition of the second red dye (sulforhodamine 101) introduces an undesired high absorbance near wavelength range of 590 nm to 605 nm, thus not providing an acceptable method of formulating references having clinically meaningful and/or normal physiological CO-ox fraction values.

In step (b), modification and manipulation of the absorption band of the red dye is conducted where the absorption peak of the red dye is shifted to a longer wavelength to more closely approximate that of blood. Upon step (b), the absorption maxima of the red dye is shifted to fall between the wavelengths of approximately 570 nm to about 585 nm. It is preferred that the shift of the absorption maxima does not inadvertently increase the absorption in the wavelength region of 590 to 605 nm. It has been found that dye(s) having an absorption maxima at wavelengths of about 350 to 450 nm are useful in step (b) because the dye(s) increase the absorbance of the spectrum at the ultraviolet region and force the absorption band of the red dye to shift toward the longer wavelength.

Preferably in step (b) is accomplished using a yellow dye (or a combination thereof) including, for example, mordant yellow 7, tartrazine, orange G, hydroxypyrenetrisulfonic acid, mordant yellow 10, combinations thereof, and so on. Particularly preferred is mordant yellow 7 dye (especially when sulforhodamine B is selected as the red dye).

Figure 3:
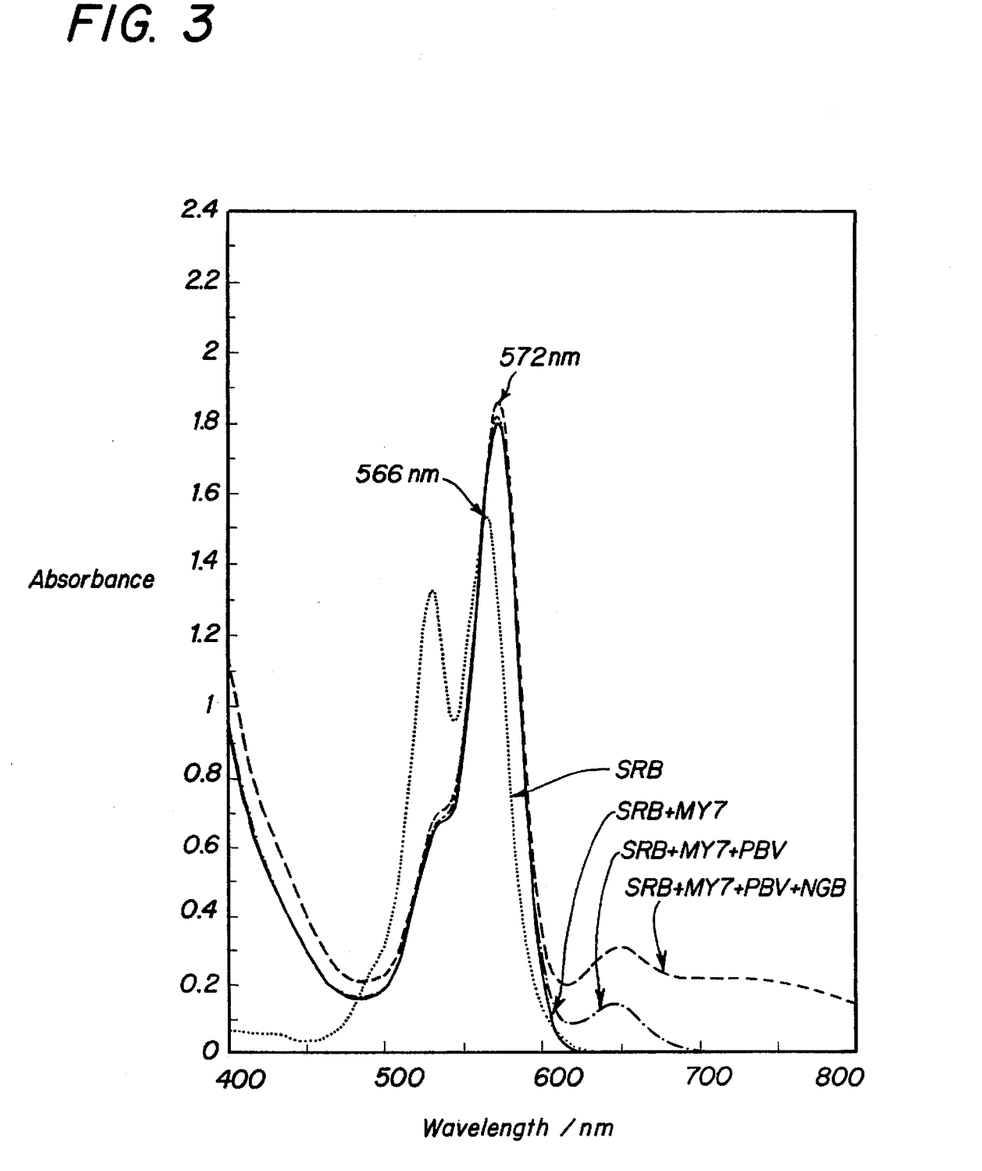
FIG. 3 illustrates spectroscopically how the spectrum of sulforhodamine B is modified using the inventive method of formulation. "SRB" is an abbreviation for sulforhodamine B; "MY7" is an abbreviation for mordant yellow 7; "PBV" is an abbreviation for patent blue violet; and "NGB" is an abbreviation for naphthol green B.

FIG. 3 illustrates the changes of the spectrum of sulforhodamine B after addition of mordant yellow 7. Spectrum 1 in FIG. 3 is the sulforhodamine B aqueous solution, and spectrum 2 is the sulforhodamine B aqueous solution containing mordant yellow 7. As shown, the original absorption peak of sulforhodamine B is shifted from 566 nm to 572 nm, with the edge of the absorption band at approximately 610 nm, and with little increase of absorbance in the wavelength range of 590 to about 605 nm.

According to the present invention, in step (c) a new relative baseline of the spectrum is established at wavelengths greater than about 640 nm and sufficient absorbance at about 630 nm is provided to yield a positive methemoglobin CO-ox fraction. Step (c) addresses that the absorbance at about 590 to about 605 nm of the dye or dye combination used in steps (a) and (b) is higher than that of normal blood. This step may be accomplished using one or more dyes. With respect to the new lifted baseline, the original absorbance can be normalized, with the normalized absorbance reduced and smaller than the original absorbance. Further, the original absorbance at about 590 to about 605 nm, although having a similar absolute absorbance value, is relatively reduced upon the establishment of the new lifted baseline. CO-oximeters take the lifted baseline from the CO-oximeters interpret the dye spectrum, and calculate the CO-ox fractions therefrom. Upon step (c), the inventive reference material will read as providing CO-ox fraction values within the instrument capability and clinically meaningful ranges, and optionally, within the normal physiological range, as described in more detail hereinafter.

One group of dyes particularly useful in step (c) are designated herein as the third dye(s). These dyes have an absorption maxima at about 625 to about 640 nm (more preferably about 630 nm) and have only minimum impact on the absorbance at wavelengths shorter than about 600 nm. Preferably, the third dye is a blue dye selected from brilliant blue FC (FD&C blue 1), erioglaucine, lissamine, alphazurine A, patent blue violet, hydroxy naphthol blue, patent blue VF, combinations thereof, and equivalents thereof (with patent blue violet, patent blue VF, and alphazurine more preferred). Patent blue violet has an absorption maxima at about 639 nm and is most preferred because it provides the absorbance not only at 630 nm, but also absorbance to some extent at a wavelength greater than 640 nm, thus generally accomplishing both functions of step (c). Adding the patent blue violet into the sulforhodamine B and yellow mordant 7 combination pushes the CO-ox fractions to the following: $O_2$Hb 80%, MetHb 15%, COHb 2% and HHb 3%, thus placing the reference material within the values set forth for instrument capability and clinically meaningful CO-ox fractions.

A second group of dyes that may be used in step (c) are designated as the fourth dye(s). These dyes have an main absorbance maxima positioned at a wavelength of from about 700 to about 780 nm and an absorption band width of from about 150 to about 200 nm. The tail of the absorption band of the dye (or dyes) of step (c) preferably lifts the baseline of the absorbance spectrum with minimal effect on absorbance at 500 to 605 nm. Preferred dyes falling within this description may be selected from any number of dyes including IR 125, naphthol green B, and combinations thereof, and so on. Most preferred is naphthol green B, having an absorption maxima at approximately 716 nm in an aqueous solution, and considered particularly effective when combined with mordant yellow 7, patent violet blue and sulforhodamine B.

For step (c) the combination of the third and fourth dyes allow the reference material containing the first and second dyes to yield CO-ox fraction values falling with the normal, physiological range. FIG. 3 exemplifies the principles of the present method of formulation. The sulforhodamine B (SRB) is the red dye that provides a basic spectrum. The addition of mordant yellow 7 (MY7) to the sulforhodamine B (SRB) modifies the spectrum by tilting the absorption band of the sulforhodamine B towards a longer wavelength and shifts the absorption maxima from about 566 nm to about 572 nm (SRB+MY7), to more closely approximate the main absorption spectrum of blood. Patent blue violet (PBV) is added for purposes of providing a spectrum absorption for methemoglobin at approximately 630 nm (SRB+MY7+ PBV) and also slightly lifts the baseline spectrum. The addition of the naphthol green B (NGB) further lifts the spectrum baseline to the right of the main absorption maxima. The ultimate result is shown by Spectrum "SRB+ MY7+PBV+NGB". In this formulation the following amounts of dyes were used: about 1.15 g/L sulforhodamine B; about 2.4 g/L mordant yellow 7; about 0.08 g/L patent blue violet; and about 1 g/L naphthol green B. When this combination was measured on a Ciba Corning M270 CO-oximeter the following CO-ox fraction ranges (which are within the normal physiological range) were provided: THb 14 g/dL, $O_2$Hb 96%, COHb 1%, MetHb 0.8% and HHb 2.2%. Providing a reference material having an oxyhemoglobin value greater than about 60 has been met with limited success in the past, however, the present invention provides a method to easily yield this objective.

Any suitable dyes may be used in the formulation of the reference materials with either aqueous or nonaqueous solvents. Water soluble dyes are particularly well-suited, including acid dyes, basic dyes, direct dyes, and so on, and equivalents thereof. The dye composition may be prepared as a dry material for ease of storage and packaging. If prepared as a dry composition, prior to usage the composition may be prepared as a solution using a suitable liquid, including water and various organic solvents, or mixtures thereof and so on, by techniques well known to those skilled in the art. It is particularly preferred that compatible dyes are used, with a particularly preferred embodiment utilizing anionic dyes. Although the method of formulating may be accomplished using various amounts of dyes, a particularly preferred composition employs a total dye concentration of from about 0.1 to about 10 mM. Further, the stability of the reference materials will be increased when high purity dyes, which are either commercially available or purified, using conventional methods known to those skilled in the art, are used in formulation.

The reference materials prepared according to the invention may be utilized on various types of optical CO-oximeters (or instruments incorporating a CO-oximeter function). Because various types of CO-oximeters may be designed and constructed to measure the absorbance of blood at different set of wavelengths, the reference materials used for these CO-oximeters will typically need dye concentration adjustment for this variation, where the adjustment may be accomplished by those skilled in the art employing the principles of this invention.

The reference materials may be prepared as calibration materials to simultaneously calibrate instrument systems that include sensors for blood gas, electrolyte, and various metabolites in addition to the CO-oximeter capability. Further, the reference materials are particularly well-suited for preparation as quality control materials for instrument systems that include a CO-oximeter capability, in addition to various other sensors, as described herein. For CO-oximeter instrument systems, ideally, the CO-ox fraction accuracy is generally checked both in the broader instrument capability CO-ox fraction range as well as in the more narrow normal physiological range (as defined herein). More preferably, the CO-oximeter instrument system is checked for performance accuracy on at least three levels. These three reference materials are preferably formulated to provide predetermined CO-ox fraction values for the total hemoglobin as well as various hemoglobin CO-ox fractions outside of and within normal physiological ranges.

Particularly preferred compositions provide a commercially acceptable stability. The stability may also extend to high temperature stability such that the composition may be autoclaved for purposes of facilitating sterilization, if desired. Additionally, the dye formulations may be prepared such that they are stable to exposure to light.

Appropriate ingredients that be included in the dye formulation preferably are those ingredients that do not interfere with the sensors of the instruments such that the reference materials may be used to provide calibration or quality control of different types of sensors simultaneously. A preferred reference prepared using the dye formulation of this invention may be prepared by combining in the appropriate relative proportions, buffer(s), dyes, sources of analytes (typically salts), and other standard chemicals commonly used in reference materials including preservatives and surfactants, and so on, as well known in the art. Buffer materials that may be used, particularly when preparing a reference standard for simultaneous usage on pH blood gas and electrolyte sensor system, are preferably selected for having a pKa close to the desired working pH. Particularly useful buffer materials are zwitterion buffers that are compatible with the selected dyes, including, for example, N-2-hyroxyethylpiperazine-N'-2-ethanesulfonic acid (HEPES), 3-(N-morpholinio)propanesulfonic acid (MOPS), Tris-(Hydroxymethyl)aminomethane (TRIS), and so on, as are well known to those skilled in the art. A combination of the salts such as, for example, NaCl, NaOH, KCl, LiCl, NaHCO$_3$, Na$_2$SO$_4$, CaCl$_2$, glucose, lithium lactate, and equivalents thereof, can be used to provide the desired concentration of electrolytes, as is well known to those skilled in the art. A stable ionized calcium concentration may be provided by using calcium chelating agents, such as, ethylenediaminetetraacetic acid (EDTA), N-hydroxyethyliminodiacetic acid (HIDA), nitrilotriacetic acid (NTA), and citric acid. Further, when providing a reference for a blood gas measurement, the desired pCO$_2$ and pO$_2$ ranges may be reached by tonometering to an equilibrium at approximately 25° C. using gas combination with proper oxygen, carbon dioxide, and nitrogen contents, as well within the skill of those trained in the art.

A particularly useful reference material includes the above-described dyes providing normal physiological CO-ox fractions while in combination with an aqueous solution of known quantities of pH, pO$_2$, pCO$_2$, Na, K, Cl, and ionized Ca iCa), glucose, and lactate (preferably in amounts that typically fall within the range of a blood sample). After said combination, the reference material may be divided into aliquots which are placed in sealed receptacles. Thereafter the receptacles may be flushed with tonometry gas, and the receptacle sealed. These references may be used for verifying the accuracy and reliability of instrument systems having multiple sensors for measuring blood pH, gas, CO-ox fractions and various electrolyte and metabolite levels. A particularly preferred embodiment that is described in TABLE A below.

TABLE A

| COMPOUND | APPROXIMATE CONCENTRATIONS |
|---|---|
| NaCl | 110 to 160 mM |
| KCl | 2.5 to 7.5 mM |
| CaCl$_2$ | 2 to 4 mM |
| HEPES | 35 to 40 mM |
| TRIS.HCl | 15 to 40 mM |
| NaOH | 20 to 50 mM |
| EDTA | 1 to 1.7 mM |
| NaHCO$_3$ | 15 to 20 mM |
| LiCl | 10 to 25 mM |
| Glucose | 0.5 to 10 g/L |
| Li lactate | 0.5 to 14 mM |
| Sulforhodamine B | 0.55 to 1.3 g/L |
| Mordant Yellow 7 | 1.4 to 3 g/L |
| Patent Blue Violet | 0.07 to 0.08 g/L |
| Naphthol Green B | 0.4 to 1.1 g/L |

To prepare clinically meaningful reference materials, preferably the first dye is used in an amount ranging from about 0.55 mM to about 4 mM; the second dye is used in an amount ranging from about 1 mM to about 10 mM; the third dye is used in an amount ranging from about 0.01 mM to 0.3 mM; and the fourth dye is used in an amount ranging from 0 to about 2.5 mM.

It is to be understood that various modifications to the invention will be apparent to and can readily be made by those skilled in the art, given the disclosure herein, without departing from the scope and materials of this invention. It is noted that the following examples given herein are intended to illustrate and not to limit the invention thereto.

EXAMPLES

Example 1

A three-level quality control standard material was prepared with varying levels of pH, pCO$_2$, pO$_2$, sodium (Na), potassium (K), chloride (Cl), ionized calcium (iCa), and three levels of total hemoglobin (THb), oxyhemoglobin (O$_2$Hb), carboxyhemoglobin (COHb), methemoglobin (MetHb), and reduced hemoglobin (HHb), as shown in TABLES I and II. The three levels prepared represent clinically significant ranges of acidosis (level a), normal or physiological (level b), and alkalosis (level c).

More particularly, three bulk solutions containing the required salts were prepared in an aqueous solution, as shown below in TABLE I.

TABLE I

| | BULK SOLUTIONS | | |
|---|---|---|---|
| COMPOUND | Level a | Level b | Level c |
| NaCl | 55.5 mM | 60 mM | 65 mM |
| KCl | 3.20 | 4.85 | 710 |
| CaCl$_2$ | 3.81 | 2.80 | 2.13 |
| NaOH | 29.5 | 38 | 34.3 |
| LiCl | 21.5 | 12.9 | — |
| EDTA | 1.63 | 1.20 | 1.14 |
| HEPES | 40 | 40 | 40 |
| TRIS.HCl | 35.5 | 15 | — |
| TRIS base | 10 | — | — |
| NaHCO$_3$ | 19.5 | 23.4 | 19.5 |

To the bulk solutions described in TABLE I, three levels of dye formulations were added, as shown in TABLE II.

TABLE II

| DYE FORMULATIONS | | | |
|---|---|---|---|
| Dye | Level a | Level b | Level c |
| Sulforhodamine B | 0.98 mM | 1.95 mM | 2.27 mM |
| Mordant Yellow 7 | 6.65 | 7.63 | 3.89 |
| Patent Blue Violet | 0.14 | 0.11 | 0.14 |
| Naphthol Green B | — | 1.10 | 0.48 |

After dyes dissolved in the bulk solution, the solutions were then tonometered at 25° C. to an equilibrium using the following gas mixtures.

TABLE III

| GAS CONCENTRATIONS (%) | | | |
|---|---|---|---|
| Gas | Level a | Level b | Level c |
| CO$_2$ | 6.10 | 3.15 | 1.77 |
| O$_2$ | 5.42 | 11.60 | 17.45 |
| N$_2$ | 88.48 | 85.25 | 80.78 |

After tonometry equilibrium was established, the pH, pO$_2$, and pCO$_2$ of the solutions remained constant even after a prolonged period of tonometry. Aliquots of the tonometered solutions were then transferred into glass ampoules while purging with the same gas mixture used in the solution tonometry. The filled ampoules were then flame-sealed.

The three levels of quality control standard having the combinations listed in TABLES I, II, and III were then evaluated by two types of instruments: ANALYZER 1=Ciba Corning M288 blood gas analyzer and ANALYZER 2=Ciba Corning M270 CO-oximeter. Results are summarized in TABLE IV.

TABLE IV

| Evaluations of Reference Standards | | | |
|---|---|---|---|
| ANALYTE | LEVEL a | LEVEL b | LEVEL c |
| ANALYZER 1 (Blood Gas) | | | |
| pH | 7.15 ± 0.02 | 7.4 ± 0.02 | 7.6 ± 0.02 |
| pCO$_2$ mm Hg | 70 ± 2 | 40 ± 2 | 21 ± 2 |
| PO$_2$ mm Hg | 63 ± 2 | 100 ± 3 | 150 ± 5 |
| Na mM | 115 ± 2 | 135 ± 2 | 155 ± 3 |
| K mM | 2.9 ± 0.3 | 4.8 ± 0.3 | 7.1 ± 0.3 |
| Cl mM | 120 ± 2 | 100 ± 2 | 80 ± 2 |
| iCa mM | 1.6 ± 0.05 | 1.15 ± 0.05 | 0.65 ± 0.05 |
| ANALYZER 2 (CO-oximeter) | | | |
| THb g/dL | 8.0 ± 0.2 | 14 ± 0.2 | 18 ± 0.2 |
| O$_2$Hb % | 78 ± 2 | 95 ± 3 | 60 ± 2 |
| COHb % | 3.5 ± 1 | 2.5 ± 1 | 6 ± 1 |
| MetHb % | 16 ± 2 | 1 ± 0.3 | 18 ± 2 |
| HHb % | 2.5 ± 1 | 1.5 ± 0.7 | 16 ± 2 |

Figure 4:
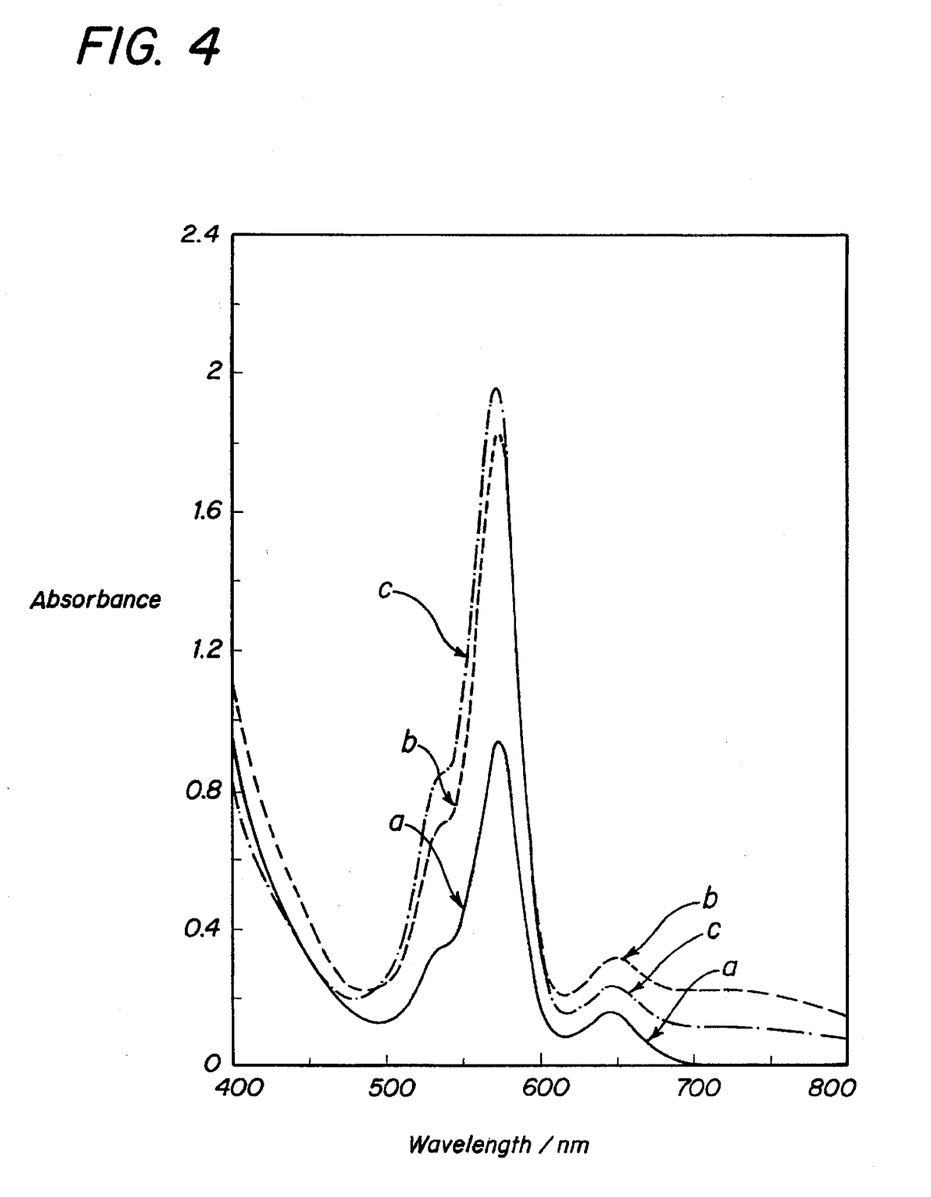
FIGS. 4–7 show the spectra of the three levels of formulations shown in Examples 1–4, respectively.

FIG. 4 provides the absorbance spectra of the three dye-based quality control standard described above, where spectrum a represents level a; spectrum b represents a level b; and spectrum c represents level c, each of which were measured using a 0.1 mm cuvette.

Example 2

A three level quality control standard was prepared by the procedure of Example 1. To the bulk solutions described in TABLE I of Example 1 the dye formulations shown in TABLE V below were added.

TABLE V

| Dye | Level a | Level b | Level c |
| --- | --- | --- | --- |
| Sulforhodamine B | 1.27 mM | 2.53 mM | 3.22 mM |
| Tartrazine | 1.34 | 1.87 | 1.60 |
| Patent Blue Violet | 0.11 | 0.17 | 0.25 |
| Naphthol Green B | 0.98 | 1.96 | 1.64 |

DYE FORMULATIONS

The formulated solutions were then tonometered at 25° C. to equilibrium using the same gas mixtures described in TABLE III of Example 1. The tonometered solutions were then transferred into glass ampoules while purging the same gas mixture used in the solution tonometry. The filled ampoules were flame-sealed. Those three levels of reference were measured in the same manner as described in Example 1. The measured ranges were similar to the data shown in Example 1.

Figure 5:
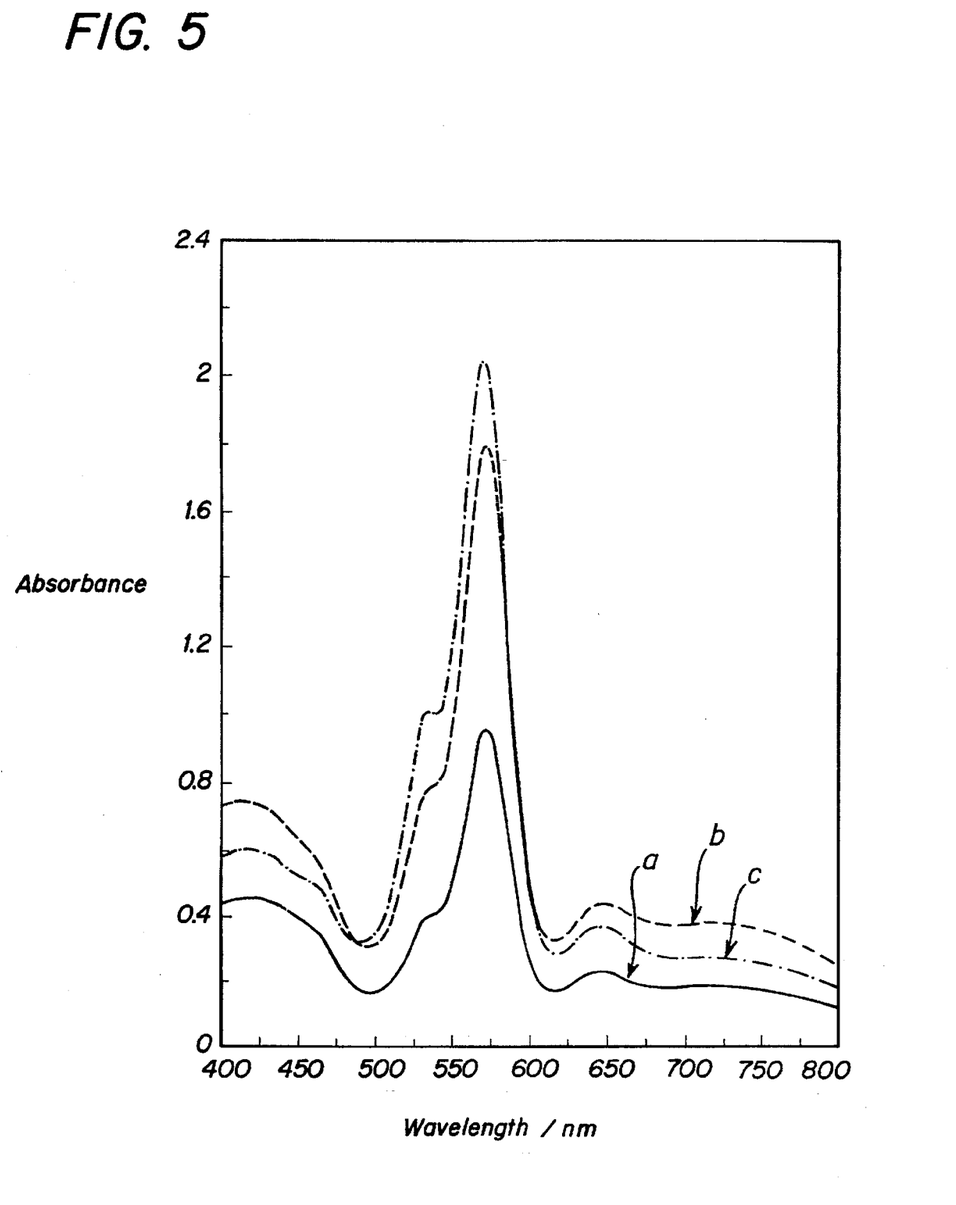

FIG. 5 provides the absorbance spectra of the three level dye-based quality control standard described above, where spectrum a represents level a; spectrum b represents a level b; and spectrum c represents level c, each of which were measured using a 0.1 mm cuvette.

Example 3

A three level quality control standard was prepared by the same procedure of Example 1. The bulk solutions of TABLE I were combined with the dye formulations of TABLE VII below.

TABLE VII

Dye Formulations

| Dye | Level a | Level b | Level c |
| --- | --- | --- | --- |
| Sulforhodamine B | 0.93 mM | 2.14 mM | 2.37 mM |
| Mordant Yellow 10 | 8.95 | 9.24 | 4.91 |
| patent blue VF | 0.12 | 0.13 | 0.08 |
| Naphthol Green B | — | 1.33 | 0.81 |

The formulated solutions were tonometered and transferred into ampoules, sealed, and thereafter measured, as described in Example 1. The data obtained using this formulation were similar to those measured in Example 1.

Figure 6:
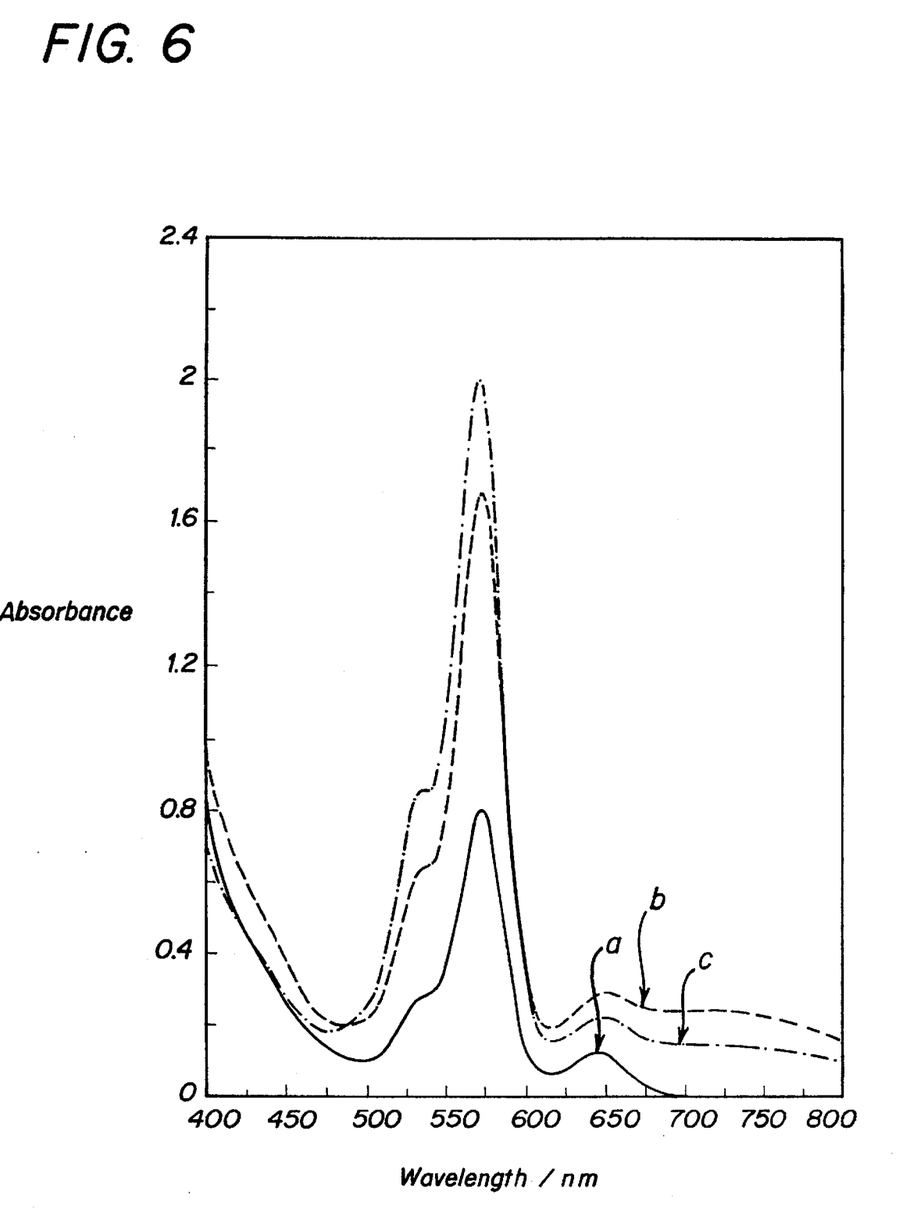

FIG. 6 provides the absorbance spectra of the three level dye-based quality control standard described above, where spectrum a represents level a; spectrum b represents a level b; and spectrum c represents level c, each of which were measured using a 0.1 mm cuvette.

Example 4

A three level quality control standard was prepared by the same procedure of Example 1. The bulk solutions of TABLE I were combined with the dye formulations of TABLE VIII below.

TABLE VIII

Dye Formulations

| Dye | Level a | Level b | Level c |
| --- | --- | --- | --- |
| Sulforhodamine B | 1.17 mM | 1.97 mM | 2.19 mM |
| Mordant Yellow 7 | 5.33 | 6.14 | 2.62 |
| FD&C Blue 1 | 0.03 | 0.04 | 0.03 |
| Naphthol Green B | 0.97 | 2.30 | 0.14 |

The formulated solutions were tonometered and transferred into ampoules, sealed, and thereafter measured, as described in Example 1. The data obtained using this formulation were similar to those measured in Example 1.

Figure 7:
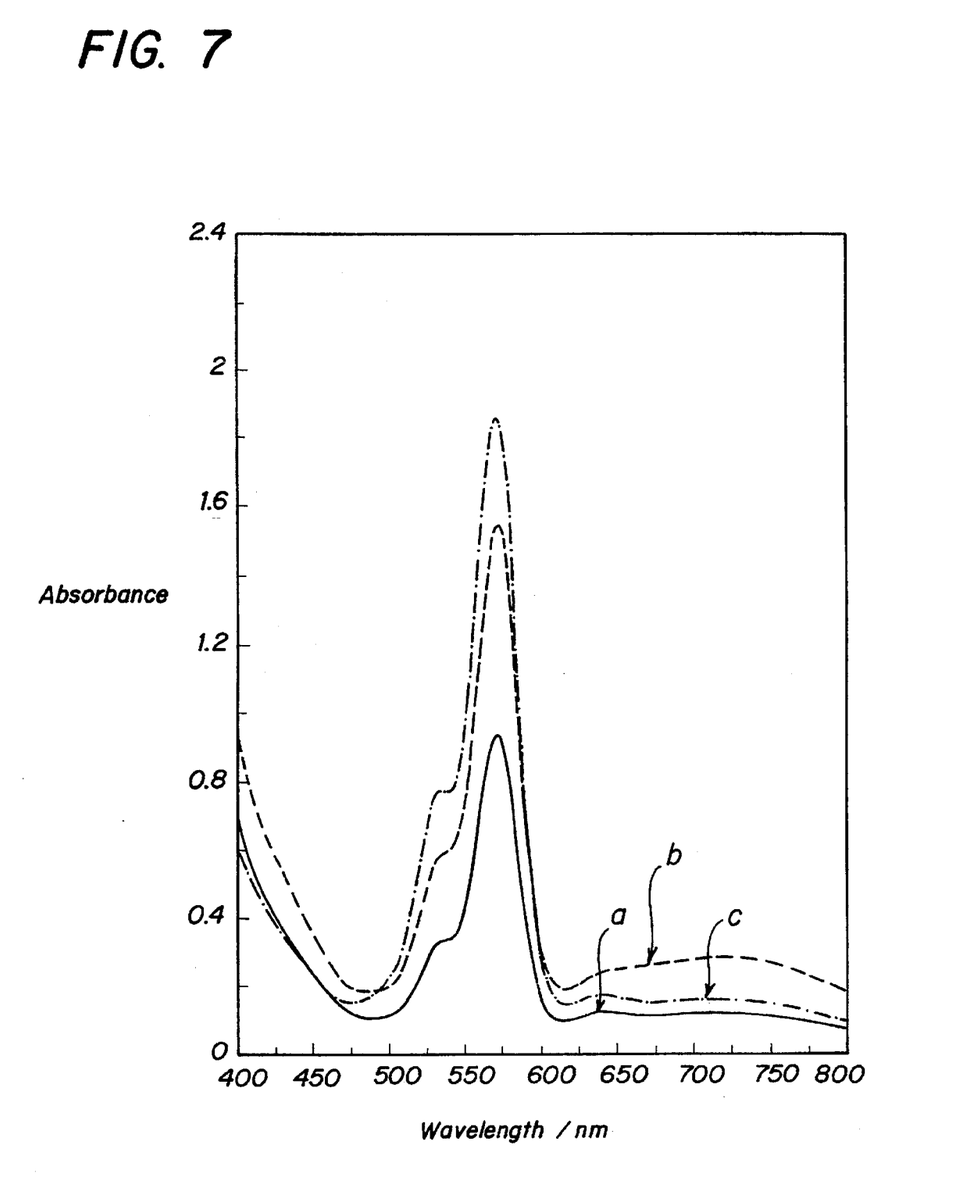

FIG. 7 provides the absorbance spectra of the three level dye-based quality control standard described above, where spectrum a represents level a; spectrum b represents a level b; and spectrum c represents level c, each of which were measured using a 0.1 mm cuvette.

That which is claimed is:

1. A reference material comprising (a) a first dye having a main absorption maxima at a wavelength between about 560 to about 580 nm wherein said first dye is a red dye selected from the group consisting of sulforhodamine B, chlorophenol red, xylenol orange, and sulforhodamine 101; (b) a second dye having an absorption maxima at a wavelength between about 350 to about 450 mn wherein said second dye is a yellow dye selected from the group consisting of mordant yellow 7, tartrazine, orange G, hydroxypyrenetrisulfonic acid, mordant yellow 10, combinations thereof; (c) a third dye having an absorption maxima at a wavelength between about 625 and about 640 nm wherein said third dye is selected from the group consisting of brilliant blue FC (FD&C blue 1), erioglaucine, lissamine, alphazurine A, patent blue violet, patent blue VF, hydroxy naphthol blue, and combination thereof; and (d) a fourth dye having an absorption maxima at a wavelength between about 700 to about 780 nm and an absorption band width of from about 150 to about 200 nm wherein said fourth dye is selected from the group consisting of IR 125, naphthol green B, and combination thereof.

2. A material according to claim 1 wherein said first dye is sulforhodamine B; said second dye is mordant yellow 7; said third dye is patent blue violet; and said fourth dye is naphthol green B.

3. A material according to claim 1 wherein said first dye is sulforhodamine B; said second dye is tartrazine; said third dye is patent blue violet; and said fourth dye is naphthol green B.

4. A material according to claim 1 wherein said first dye is sulforhodamine B; said second dye is mordant yellow 10; and said third dye is patent blue VF; and said fourth dye is naphthol green B.

5. A material according to claim 1 wherein said first dye is sulforhodamine B; said second dye is mordant yellow 7; and said third dye is FD&C blue 1; and said fourth dye is naphthol green B.

6. A material according to claim 1 wherein the first dye is used in an amount ranging from about 0.55 mM to about 4 mM; the second dye is used in an amount ranging from about 1 mM to about 10 mM; the third dye is used in an amount ranging from about 0.01 mM to 0.3 mM; and the fourth dye is used in an amount ranging from 0 to about 2.5 mM.

7. A material according to claim 1 comprising the following:

| COMPOUND | CONCENTRATIONS |
|---|---|
| NaCl | 110 to 160 mM |
| KCl | 2.5 to 7.5 mM |
| $CaCl_2$ | 2 to 4 mM |
| HEPES | 35 to 40 mM |
| TRIS.HCl | 15 to 40 mM |
| NaOH | 20 to 50 mM |
| EDTA | 1 to 1.7 mM |
| $NaHCO_3$ | 15 to 20 mM |
| LiCl | 10 to 25 mM |
| Glucose | 0.5 to 10 g/L |
| Li lactate | 0.5 to 14 mM |
| Sulforhodamine B | 0.55 to 1.3 g/L |
| Mordant Yellow 7 | 1.4 to 3 g/L |
| Patent Blue Violet | 0.07 to 0.08 g/L |
| Naphthol Green B | 0.4 to 1.1 g/L. |

8. A material according to claim 7 wherein said reference material provides clinical hemoglobin fractions of: about 60% to about 98% oxyhemoglobin; from 0 to about 20% carboxyhemoglobin; from 0 to about 20% methemoglobin; and from 0 to about 20% reduced hemoglobin.

9. A material according to claim 7 wherein said reference material provides physiological hemoglobin fractions of: oxyhemoglobin 94–98%, carboxyhemoglobin 0 about 1%, methemoglobin 0 to about 1.5%, and reduced hemoglobin from about 1 to about 5%.

10. A method for quality control of hemoglobin instrument systems comprising: (1) subjecting said instrument to quality control standard material comprising (a) a first dye having a main absorption maxima at a wavelength between about 560 to about 580 nm; (b) a second dye having an absorption maxima at a wavelength between about 350 to about 450 nm; and (c) a third dye having an absorption maxima at a wavelength between about 625 and about 640 nm; and (d) a fourth dye having an absorption maxima at a wavelength between about 700 to about 780 nm and an absorption band width of from about 150 to about 200 nm; wherein said dyes are used in a sufficient amount to provide said control with a pre-determined level of hemoglobin fractions; (2) obtaining an instrument measurement of hemoglobin fractions of said control; and (3) comparing said instrument measurement off said hemoglobin fractions of said control with said predetermined level of hemoglobin fractions to check the accuracy of said instrument, wherein said quality control standard material is prepared with at least three levels and wherein at least one level has said fourth dye, said three levels of quality control standard material comprising the following:

| Dye | Level a | Level b | Level c |
|---|---|---|---|
| Sulforhodamine B | 0.98 mM | 1.95 mM | 2.27 mM |
| Mordant Yellow 7 | 6.65 | 7.63 | 3.89 |
| Patent Blue Violet | 0.14 | 0.11 | 0.14 |
| Naphthol Green B | 0 | 1.10 | 0.48. |

11. A method for quality control of hemoglobin instrument systems comprising: (1) subjecting said instrument to a quality control standard material comprising: (a) a first dye having a main absorption maxima at a wavelength between about 560 to about 580 nm; (b) a second dye having an absorption maxima at a wavelength between about 350 to about 450 nm; and (c) a third dye having an absorption maxima at a wavelength between about 625 and about 640 nm; and (d) a fourth dye having an absorption maxima at a wavelength between about 700 to about 780 nm and an absorption band width of from about 150 to about 200 nm; wherein said dyes are used in a sufficient amount to provide said control with a pre-determined level of hemoglobin fractions; (2) obtaining an instrument measurement of hemoglobin fractions of said control; and (3) comparing said instrument measurement of said hemoglobin fractions of said control with said predetermined level of hemoglobin fractions to check the accuracy of said instrument, wherein said quality control standard material is prepared with at least three levels and wherein at least one level has said fourth dye, said three levels of quality control standard material comprising the following:

| Dye | Level a | Level b | Level c |
|---|---|---|---|
| Sulforhodamine B | 1.27 mM | 2.53 mM | 3.22 mM |
| Tartrazine | 1.34 | 1.87 | 1.60 |
| Patent Blue Violet | 0.11 | 0.17 | 0.25 |
| Naphthol Green B | 0.98 | 1.96 | 0.64. |

12. A method for quality control of hemoglobin instrument systems comprising: (1) subjecting said instrument to a quality control standard material comprising (a) a first dye having a main absorption maxima at a wavelength between about 560 to about 580 nm; (b) a second dye having an absorption maxima at a wavelength between about 350 to about 450 nm; and (c) a third dye having an absorption maxima at a wavelength between about 625 and about 640 nm; and (d) a fourth dye having an absorption maxima at a wavelength between about 700 to about 780 mn and an absorption band width of from about 150 to about 200 nm; wherein said dyes are used in a sufficient amount to provide said control with a pre-determined level of hemoglobin fractions; (2) obtaining an instrument measurement of hemoglobin fractions of said control: and (3) comparing said instrument measurement of said hemoglobin fractions of said control with said predetermined level of hemoglobin fractions to check the accuracy of said instrument, wherein said quality control standard material is prepared with at least three levels and wherein at least one level has said fourth dye said three levels of quality control standard material comprising the following:

| Dye | Level a | Level b | Level c |
|---|---|---|---|
| Sulforhodamine B | 1.17 mM | 1.97 mM | 2.19 mM |
| Mordant Yellow 7 | 5.33 | 6.14 | 2.62 |
| FD&C Blue 1 | 0.03 | 0.04 | 0.03 |
| Naphthol Green B | 0.97 | 2.30 | 0.14. |

13. A method for quality control of hemoglobin instrument systems comprising: (1) subjecting said instrument to a quality control standard material comprising (a) a first dye having a main absorption maxima at a wavelength between about 560 to about 580 nm; (b) a second dye having an absorption maxima at a wavelength between about 350 to about 450 nm; (c) a third dye having an absorption maxima at a wavelength between about 625 to about 640 nm; and a fourth dye having an absorption maxima at a wavelength between about 700 to about 780n m and an absorption band width of from about 150 to about 200 nm; wherein said dyes are used in a sufficient amount to provide said control with a predetermined level of hemoglobin fractions; (2) obtaining an instrument measurement of hemoglobin fractions of said control, and (3) comparing said instrument measurement of said hemoglobin fractions of said control with said predetermined level of hemoglobin fractions to check the accuracy of said instrument, wherein said quality control standard material is prepared with at least three levels and wherein at least one level has said fourth dye, said three levels of quality control standard material comprising the following:-

| Dye | Level a | Level b | Level c |
|---|---|---|---|
| Sulforhodamine B | 1.17 mM | 1.97 mM | 2.19 mM |
| Mordant Yellow 7 | 5.33 | 6.14 | 2.62 |
| FD&C Blue 1 | 0.03 | 0.04 | 0.03 |
| Naphthol Green B | 0.97 | 2.30 | 0.14. |

* * * * *